(12) United States Patent
Sauer

(10) Patent No.: US 8,016,845 B1
(45) Date of Patent: Sep. 13, 2011

(54) INSTRUMENT FOR GUIDING THE SURGICAL CUTTING OF TISSUE AND METHOD OF USE

(75) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 1255 days.

(21) Appl. No.: 10/772,185

(22) Filed: Feb. 4, 2004

Related U.S. Application Data

(60) Provisional application No. 60/444,938, filed on Feb. 4, 2003.

(51) Int. Cl.
*A61B 17/32* (2006.01)

(52) U.S. Cl. .......................... 606/170; 604/22

(58) Field of Classification Search .......... 606/159, 606/170, 171, 180, 167, 176; 604/22; 600/564, 600/565
See application file for complete search history.

(56) References Cited

U.S. PATENT DOCUMENTS

| | | | | |
|---|---|---|---|---|
| 2,873,742 | A * | 2/1959 | Shelden | 128/207.29 |
| 3,802,438 | A * | 4/1974 | Wolvek | 606/232 |
| 4,628,929 | A * | 12/1986 | Intengan et al. | 606/182 |
| 4,631,052 | A | 12/1986 | Kensey | |
| 4,867,157 | A | 9/1989 | McGurk-Burleson et al. | |
| 4,883,458 | A * | 11/1989 | Shiber | 604/22 |
| 4,979,951 | A | 12/1990 | Simpson | |
| 5,074,841 | A | 12/1991 | Ademovic et al. | |
| 5,078,722 | A * | 1/1992 | Stevens | 606/159 |
| 5,084,010 | A | 1/1992 | Plaia et al. | |
| 5,419,774 | A | 5/1995 | Willard et al. | |
| 5,429,136 | A | 7/1995 | Milo et al. | |
| 5,431,666 | A | 7/1995 | Sauer et al. | |
| 5,520,702 | A | 5/1996 | Sauer et al. | |
| 5,562,686 | A | 10/1996 | Sauer et al. | |
| 5,562,694 | A * | 10/1996 | Sauer et al. | 606/176 |
| 5,624,457 | A | 4/1997 | Farley et al. | |
| 5,632,754 | A | 5/1997 | Farley et al. | |
| 5,643,289 | A | 7/1997 | Sauer et al. | |
| 5,643,296 | A | 7/1997 | Hundertmark et al. | |
| 5,766,183 | A | 6/1998 | Sauer | |

(Continued)

FOREIGN PATENT DOCUMENTS

DE  89 00 059.5  1/1989

OTHER PUBLICATIONS

Brochure entitled "SEW-RIGHT SR 5, The Single Squeeze Suturing Device", LSI Solutions, Copyright 2000.

(Continued)

*Primary Examiner* — Victor Nguyen
(74) *Attorney, Agent, or Firm* — Kenneth J. LuKacher

(57) ABSTRACT

An instrument is provided for cutting tissue having a housing, a shaft extending from the housing to a distal end with an opening, and a guide tube extending from the distal end through the opening for receiving a guide wire through the shaft and housing. A movable blade shuttle having a blade is provided at the distal end. The blade shuttle's travel is guided by the guide tube when the blade shuttle and blade is extended from the distal end opening to cut tissue and retracted back through the distal end opening. The housing has a pivotal actuator member mechanically coupled to the blade shuttle to remotely control movement of the blade shuttle at the instrument's distal end. The instrument may be used for longitudinal cutting of tissue at remote sites in the body of a patient to provide incisions of precise depth and length over a controlled path of a guide wire.

25 Claims, 18 Drawing Sheets

U.S. PATENT DOCUMENTS

| | | | | |
|---|---|---|---|---|
| 5,817,013 | A * | 10/1998 | Ginn et al. | 600/114 |
| 6,036,707 | A * | 3/2000 | Spaulding | 606/159 |
| 6,368,334 | B1 * | 4/2002 | Sauer | 606/139 |
| 2002/0016624 | A1 | 2/2002 | Patterson et al. | |
| 2002/0107530 | A1 | 8/2002 | Sauer et al. | |

OTHER PUBLICATIONS

Desai, M. et al., Percutaneous Endopyeloplasty: A Novel Technique, Journal of Endourology, vol. 16, No. 7, pp. 431-443, Sep. 2002.

Gill, I. et al., Percutaneous Endopyeloplasty: Description of a New Technique, Journal of Urology, vol. 168, No. 5, pp. 2097-2102, Nov. 2002.

Applied Medical, Acucise Endopyelotomy/Endoureterotomy, printout of web page at: http://www.appliedmed.com/professionals/procedure_detail.aspx?proceGroupID=4&proceID=29&Title=Acucise+Endopyelotomy+%2f+Endoureterotomy, Jun. 18, 2004.

* cited by examiner

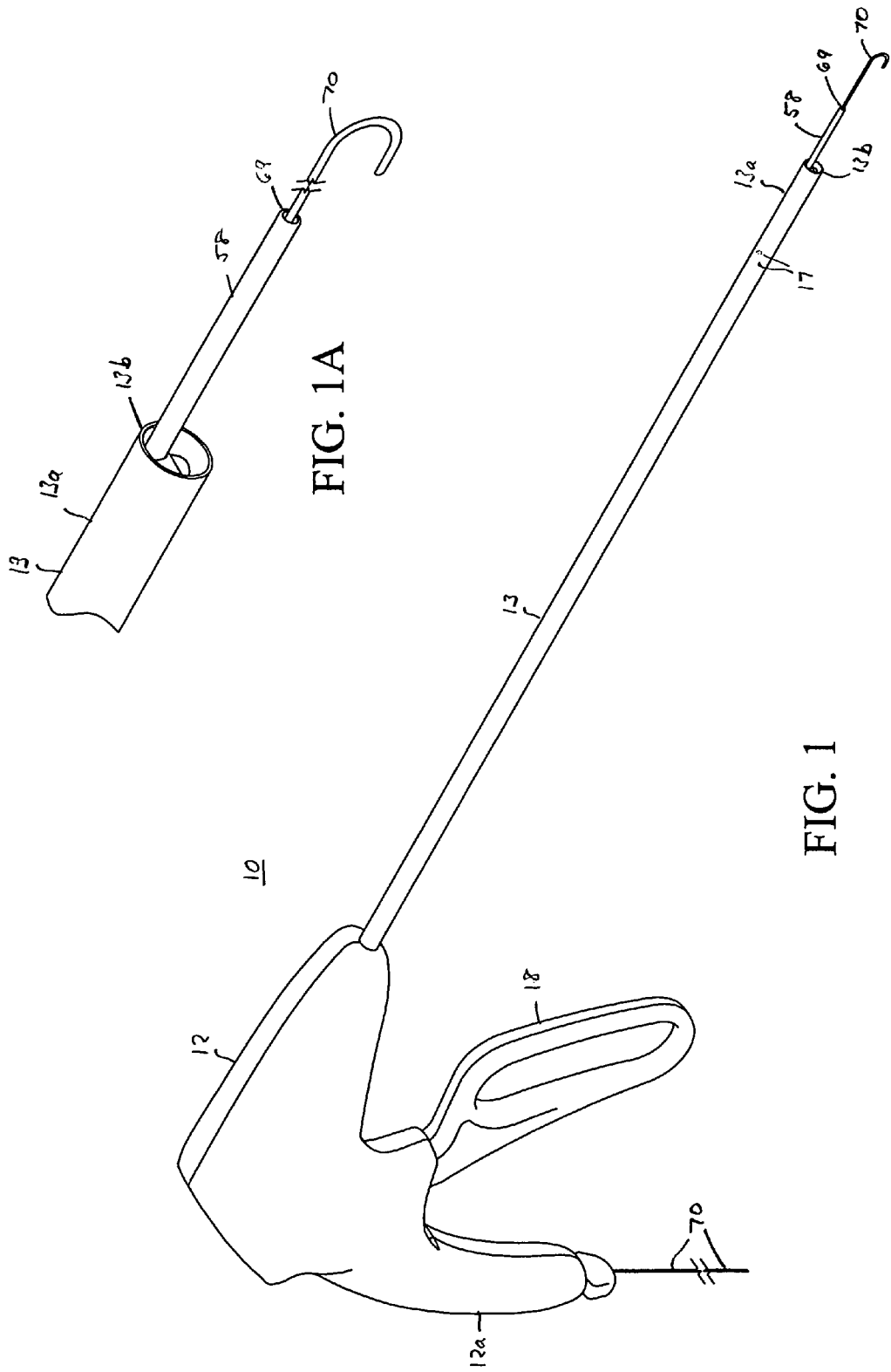

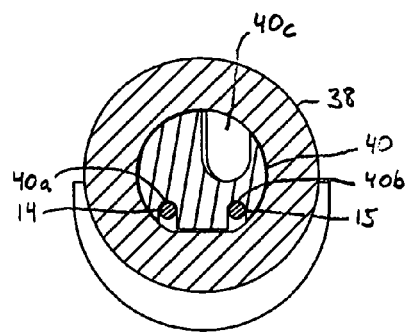
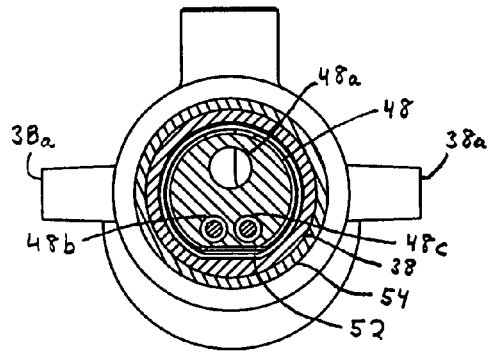
FIG. 6  FIG. 7
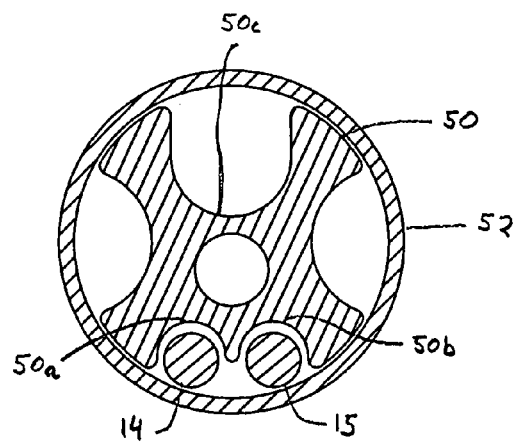
FIG. 8

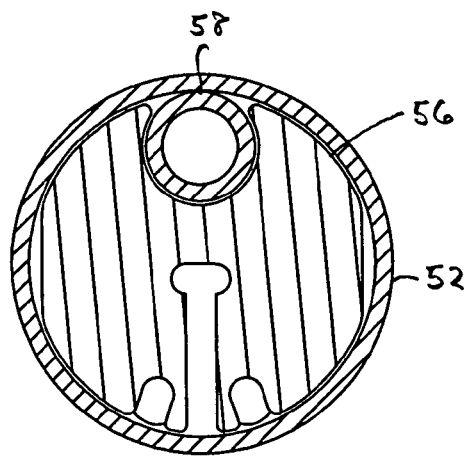
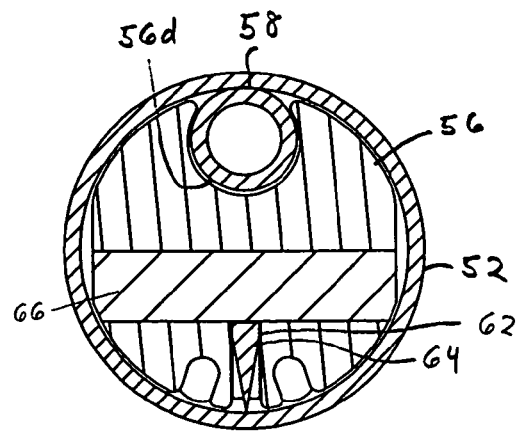
FIG. 12  FIG. 13
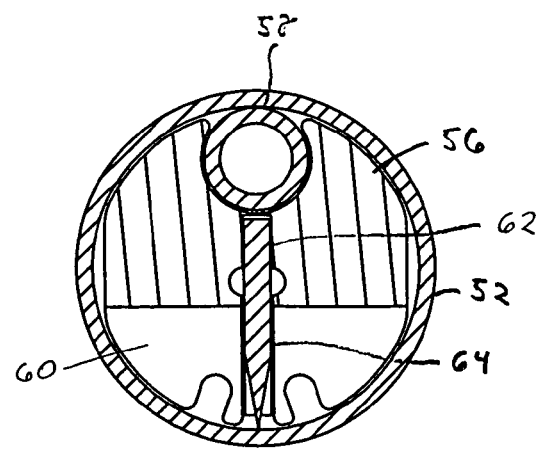
FIG. 14

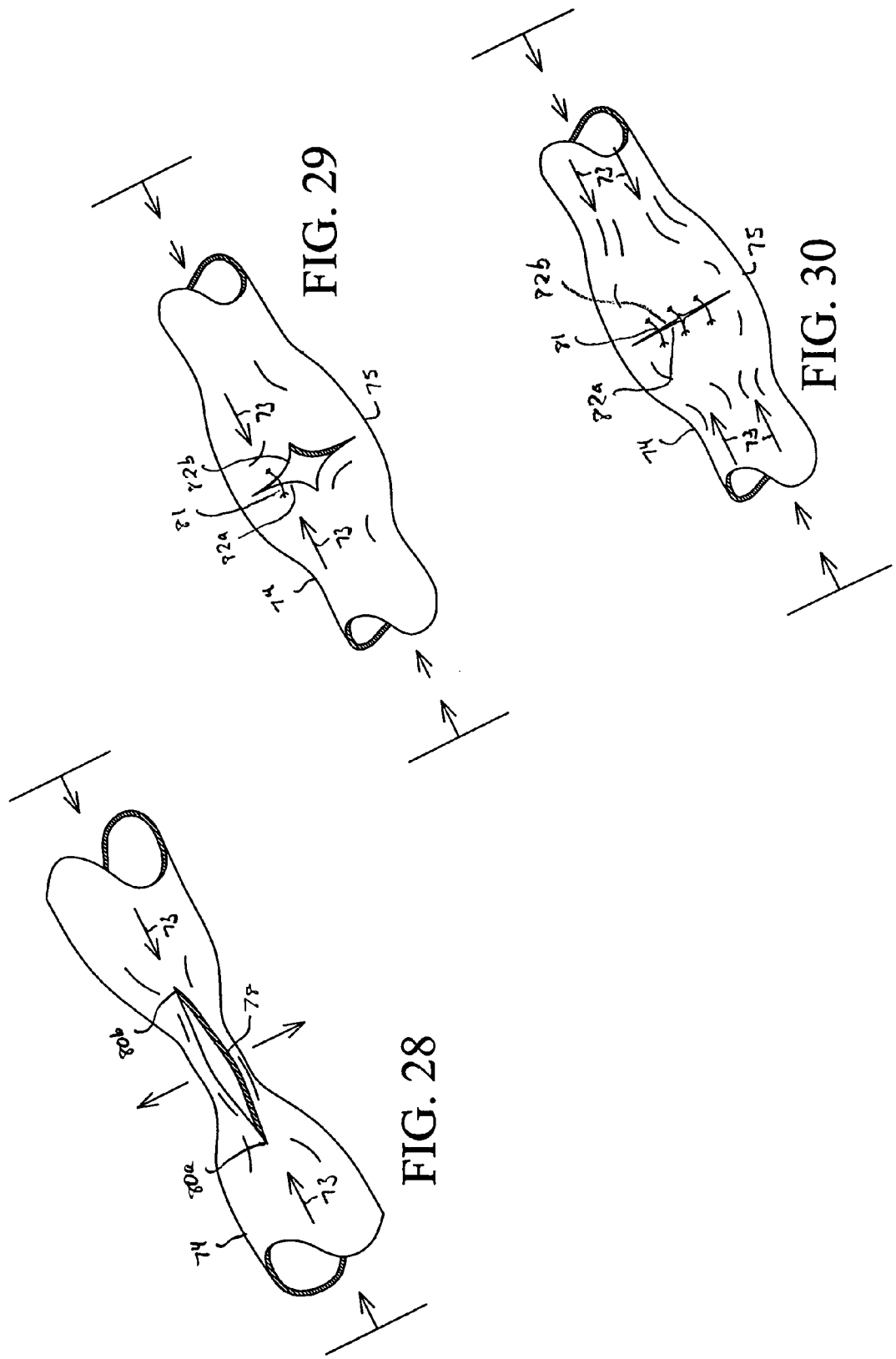

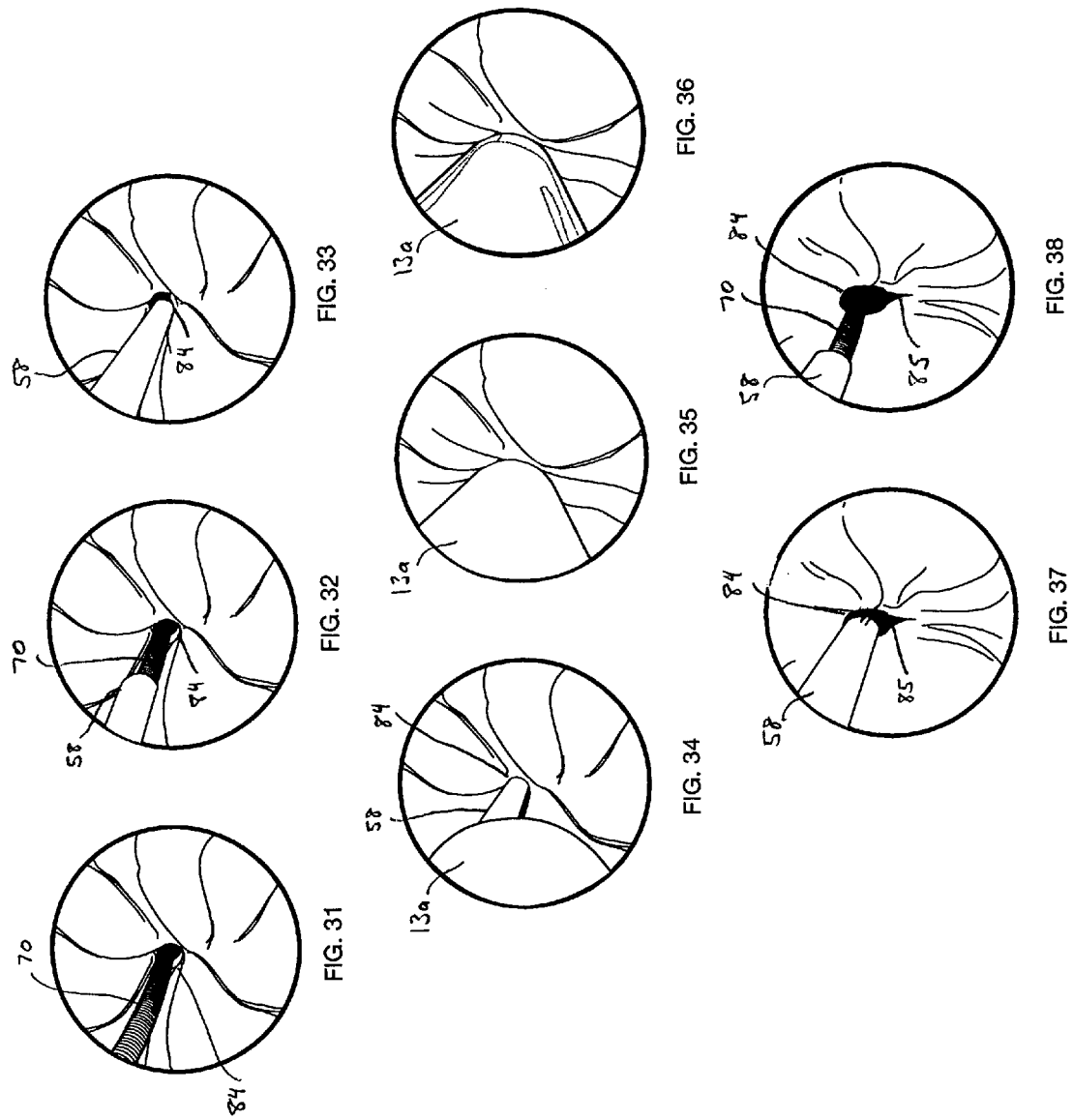

INSTRUMENT FOR GUIDING THE SURGICAL CUTTING OF TISSUE AND METHOD OF USE

This application claims the benefit of priority to U.S. Provisional Patent Application No. 60/444,938, filed Feb. 4, 2003, which is herein incorporated by reference.

FIELD OF THE INVENTION

The present invention relates to an instrument and method for surgically cutting tissue in the body of a patient, and in particular to the remote surgical cutting of tissue in the body of the patient to a precise depth, length and along a controlled path. The invention is useful for the surgically cutting tissue from sites in the body including, for example, the lining of tubular structures, such as in the genitourinary tract (e.g., at a narrow or stenotic ureteral pelvic junction), the biliary tract (e.g., at a common bile duct stricture) or the gastrointestinal tract (e.g., at an esophageal stricture), or within soft tissue structures or at the surface of soft tissue structures (e.g., at the surface of the liver or eyeball), or from within soft tissue structures (e.g., within the breast or brain tissue).

BACKGROUND OF THE INVENTION

Simple instruments, such as scalpels and scissors, have been used throughout the history of medicine for cutting tissue. Other cutting devices have been developed for manually cutting or slicing tissue or for more automated cuts (e.g., circular blades for end-to-end anastomotic staplers) or even lasers for cutting tissue structures using electromagnetic energy. However, such cutting devices have not provided a simple, precise way of accurately guiding a cutting blade at remote structures. Guide wires are used in many medical techniques. For example, a cautery wire on a balloon is used to burn through tissue, such as in a product called Acucise® (sold by Applied Medical Resources Corp. of Rancho Santa Margarita, Calif.). This balloon device's use of electrocautery to burn open wounds is sometimes contraindicated for optimized wound healing; it is also somewhat cumbersome to use and is quite expensive. While such devices may be useful in their particular applications, they do not generally control for the precise, optimized cutting of tissue at a remote site utilizing a blade that can be guided along the intended path with accuracy and control.

A disease process of often unclear etiology can occur in patients at the junction of the ureter and the renal pelvis, (i.e., commonly called the UPJ) leading to the narrowing of the proximal ureter and causing an obstruction of urine flow out of the renal pelvis. Such urinary flow obstruction can cause a painful disease state, called hydronephrosis. Varying degrees of relief for this pathologic process can be realized through surgery using longitudinal incisions in the ureteral wall through the length of the stricture or cutting the entire diseased section away and suturing the ureter back onto the renal pelvis. Completely transecting the ureter off of the renal pelvis and surgically reattaching it using sutures is a procedure called amputation pyeloplasty; this amputation pyeloplasty approach usually requires a sophisticated, major open operation. A less invasive, alternative method is to create a longitudinal oriented incision in the narrowed ureter to relieve the obstruction and it can be further enhanced by a suture closure of the longitudinal incision in a transverse fashion. This longitudinal to transverse wound closure approach is often called a Heineke-Mikulicz technique and in the application of the sutured closure of the stenotic renal pelvis is called a Fenger-plasty. Leaving the ureteral incision unclosed (i.e., a pyelotomy) results in a 10% to 15% reduction in long-term relief of the obstructive symptoms when compared to a sutured closure (i.e., a pyeloplasty). The Acucise® balloon may be used for simply cutting open the ureter for a pyelotomy. Research has been conducted toward improving suturing such wound closures together using automated suturing technologies. The SEW-RIGHT® SR 5® (SEW-RIGHT® produced by LSI SOLUTIONS, Inc., Victor, N.Y.) in a pre-clinical porcine model is described in the *Journal of Endourology* (Desai M M, Gill I S, Carvalhal E F, Kaouk J H, Banks K, Raju R, Raja S S, Meraney A M, Sung G T, Sauer J S: Percutaneous Endopyeloplasty: A Novel Technique. Volume 16, Number 7, September 2002, Pages 431-443). Subsequent clinical applications of this suturing approach were published in the *Journal of Urology* (Gill I S, Desai M M, Kaouk J H, Wani K, Desai M R: Percutaneous Endopyeloplasty: Description of a New Technique. Volume 168, Number 5, November 2002, Pages 2097-2102). As a result of this research, it became evident of a need for improved incising these openings in the strictured ureters, which can also be used in other tubular tissue structures.

SUMMARY OF THE INVENTION

The principal object of the present invention is to provide an instrument and method for the remote guided surgical cutting of tissue structures along a prescribed path at a predetermined incision depth and controlled length.

It is another object of the present invention to provide an instrument and method having a controlled cutting of tissue using a blade shuttle passed over a guide wire to cut tissue.

It is still another object of the present invention to provide an instrument and method which enables the remote controlled cutting of soft tissue structures and provides a shielded blade for transmission of the instrument through other instruments, such as endoscopes.

Briefly described, the present invention embodies an instrument having a housing and a rigid or flexible shaft extending from the housing to the distal end. The distal end of the shaft has an opening from which a smaller stationary guide tube extends. The guide tube can also receive a guide wire, which can be passed through the entire length of the instrument and simultaneously through tissue structures in a patient's body. The distal end of the instrument is insertable over a guide wire into remote regions of tissue that may be narrowed or otherwise pathologic and requiring incision. An actuator member (e.g., lever and a handle) at the housing in mechanically coupled to a blade shuttle movable at the distal end through the distal end opening to drive the blade shuttle forward or backward. By squeezing the actuator member, the blade shuttle with an integrated blade is advanced out from the instrument's shaft and guided along the guide tube to traverse the tissue site and precisely incise an opening. The blade shuttle and blade are retracted back into the instrument shaft by release of the actuator member. The depth, length and path of the cut can thereby be precisely controlled to enable an accurate incision of otherwise relative inaccessible tissue.

Tissue incised by the instrument may be left to heal by secondary intention or mechanically closed, such as by suture, to appose wound edges for the induction of primary healing.

This instrument may be applied in narrowed region of a tubular structure at remote sites in the body of a patient, such as in the urinary tract, biliary tract, gastrointestinal structures or along any tissue surface or soft tissue structure in the body. Also, the instrument can be used for cutting tissue for biopsy specimens, or other surgical applications where longitudinal incisions are needed. In the urinary tract, the present invention may be used through a percutaneous access approach to the kidney of a patient, to provide an appropriate coaxial tracking of a cutting blade along the axis of the stenotic ureter segment.

A method for using the instrument is also provided by passing a guide wire through the instrument's shaft from the distal end thereof, guiding the distal end of the instrument adjacent the tissue to be cut with the aid of the guide wire, extending a blade from the distal end of the instrument to provide a longitudinally incision in the tissue, and then retracting the blade from the distal end.

BRIEF DESCRIPTION OF THE DRAWINGS

From the foregoing objects, features and advantages of the invention will become more apparent from a reading of the following description in connection with the accompanying drawings, in which:

FIG. 1 is a perspective view of the instrument of the present invention with its actuator member in the forward position and the blade shuttle of the instrument retracted fully back within the instrument;

FIG. 1A is an enlarged partial view of the distal end of the instrument of FIG. 1;

FIG. 6 is a cross-sectional view along lines 6-6 of the instrument of FIG. 4;

FIG. 7 is a cross-sectional view along lines 7-7 of the instrument of FIG. 4;

FIG. 8 is a cross-sectional view along lines 8-8 of the instrument of FIG. 4;

FIG. 12 is a cross-sectional view along lines 12-12 of the instrument of FIG. 4;

FIG. 13 is a cross-sectional view along lines 13-13 of the instrument of FIG. 4;

FIG. 14 is a cross-sectional view along lines 14-14 of the instrument of FIG. 4;

FIG. 15 is an exploded view of the assembly of the distal end of the instrument of FIG. 5 from a different perspective;

FIG. 28 is a partial perspective view of a longitudinal incision in a tubular structure along a narrowing of the tubular structure such as placed by the instrument of FIG. 1 in the tubular structure as shown, for example, in FIGS. 21-27;

FIG. 29 is another partial perspective view similar to FIG. 28 showing the pulling of the proximal and distal margins of the wound together to provide for more luminal diameter;

FIG. 30 is another partial perspective view similar to FIG. 29 showing a sutured closure of the tubular structure to add increased diameter at the expense of structure length;

FIG. 31 is a nephroscopic view of an ureteropelvic junction with a guide wire extending out from the ureteral opening of a patient;

FIG. 32 is a nephroscopic view of the ureteropelvic junction similar to FIG. 31 with the guide tube of the instrument of FIG. 1 being advanced over a guide wire toward the ureter;

FIG. 33 is a nephroscopic view of the ureteropelvic junction similar to FIG. 32 with the guide tube of the instrument of FIG. 1 over a guide wire about to enter the ureter;

FIG. 34 is a nephroscopic view of the ureteropelvic junction similar to FIG. 33 with the guide tube of the instrument of FIG. 1 entering the ureter;

FIG. 35 is a nephroscopic view of the ureteropelvic junction similar to FIG. 34 with the shaft of the instrument of FIG. 1 abutted against the proximal ureteral opening;

FIG. 36 is a nephroscopic view of the ureteropelvic junction similar to FIG. 35 during the advancing and retraction of the blade shuttle and blade of the instrument of FIG. 1;

FIG. 37 is a nephroscopic view of the ureteropelvic junction similar to FIG. 36 with the guide tube of the instrument of FIG. 1 exiting the incised ureter; and FIG. 38 is a nephroscopic view of the ureteropelvic junction similar to FIG. 37 showing the guide wire in the incised ureter while the instrument of FIG. 1 is being retracted from the site.

DETAILED DESCRIPTION OF THE INVENTION

Figures 2, 2A:
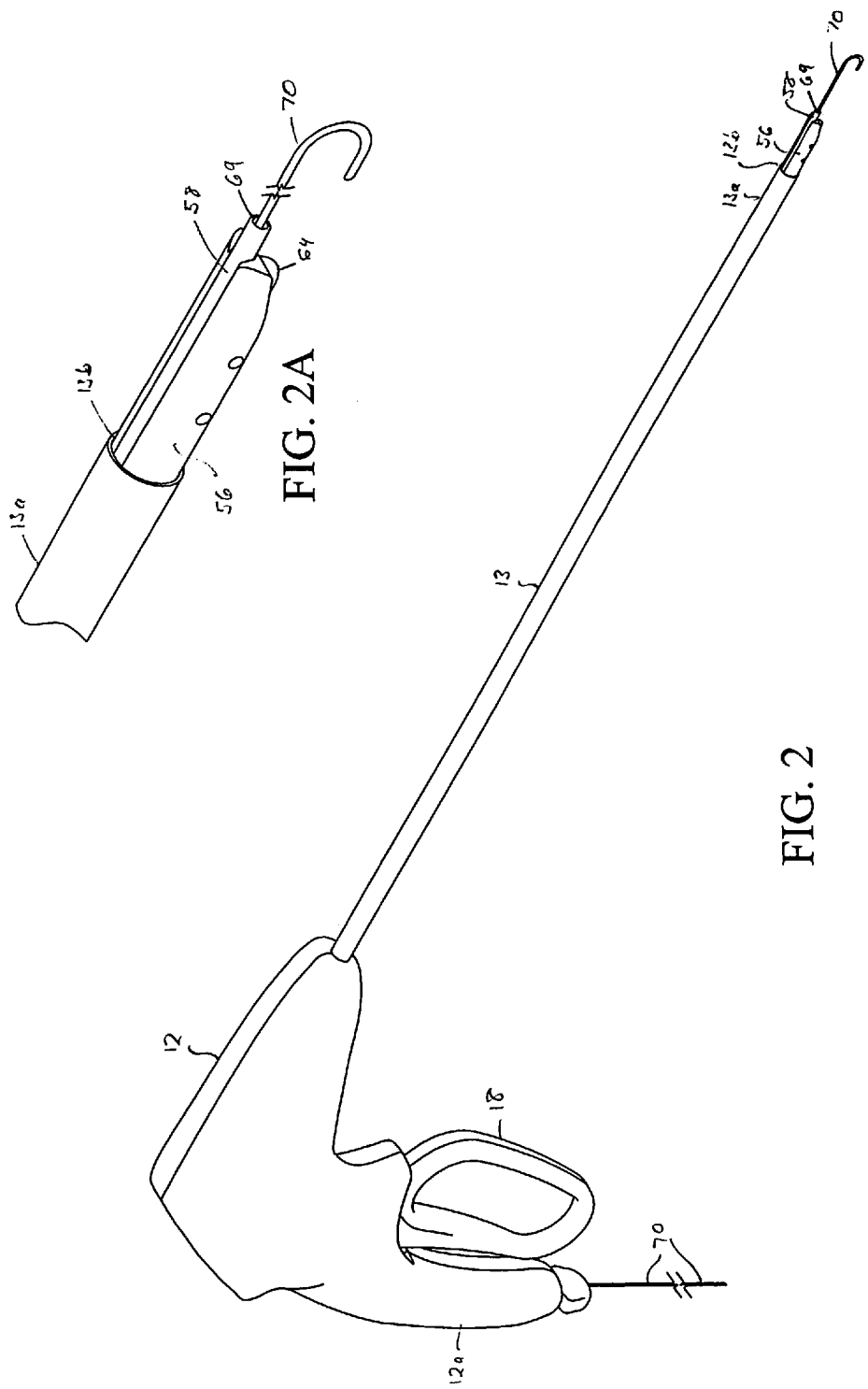
FIG. 2 is a perspective view of the instrument of FIG. 1 with its actuator member in the back position and the blade shuttle fully advanced over the tube guide of the instrument.
FIG. 2A is an enlarged partial view of the distal end of the instrument of FIG. 2.

Referring to the FIGS. 1-17, the instrument 10 of the present invention is shown. The instrument 10 has a housing 12 with a body shaped like a pistol having a handle portion 12a, and may be made of a two-piece construction of molded plastic. A shaft 13 extends from an opening 12e of the housing to a distal end. The shaft 13 represents an assembly of components described below. A pair of drive rods (or wires) 14 and 15 extend from housing 12 through the shaft 13 to the distal end 13a of the shaft, which has a distal opening 13b. Each drive rod 14 and 15 has a first end in the housing having a spherical member 16a and 16b, respectively, attached thereto, such as a ball or bearing. Both drive rods 14 and 15 and spherical members 16a and 16b may be made of metal, such as surgical stainless steel. The spherical member 16a and 16b may have a bore into which the first ends of the drive rods 14 and 15, respectively, extend and joined thereto, such as by welding or brazing.

The instrument 10 includes an actuator member 18 representing a lever having two pins 20 extending into holes 19 in the sides of housing 12 upon which the actuator member 18 is pivotally mounted in the housing. Actuator member 18 has a handle portion 12a which extends through an opening 12c in housing 12 to enable pivotal movement about pins 20. An extension spring 22 is provided which hooks at one end in a notch 23 of actuator member 18 and is wound at the other end around a pin 24 located in holes 19a in the sides of housing 12, such that the actuator member 18 is spring biased to retain actuator member 18 normally in a forward position, as shown in FIG. 1. The body of housing 12 has a front portion 12d providing a stop that limits the pivotal movement of the actuator member 18. A notch 26 is provided at the top of the actuator member which is shaped to receive the first ends of rods 14 and 15, i.e., spherical members 16a and 16b, to be driven forward by an operator pulling actuator member 18 to pivot actuator member 18 towards handle portion 12a, as shown for example in FIG. 2. Two grooves 28 are provided by three fingers 30 into which the rods 14 or 15 near the spherical members 16a and 16b, respectively, extend.

A retainer member 32 is fixed in housing 12 by two flanges 32a above actuator member 18. The retainer member has two grooves 34 formed by fingers 35 through which rods 14 and 15 extend. The lower surface 32b of retainer member 32 is curved and faces correspondingly curved upper surface 37 of actuator member 18, such that the actuator member is slidable along lower surface 32b responsive to the operator pulling or releasing the actuator member.

An adapter 38 is mounted in housing 12 by two flanges 38a. The adapter 38 has a bore 38b extending there through in which a rod spreader 40 is located. Rod spreader 40 has two channels 40a and 40b into which rods 14 and 15 are respectively located to increase the distance between the rods 14 and 15 as they extend toward notch 26 of the actuator member 18, such that the rods are properly aligned to grooves 28 of the actuator member 18. A cross-section through rod spreader 40 and adapter 38 is shown in FIG. 6.

A tube 42 is provided for passage of a guide wire in housing 12. Tube 42 has one end received in an opening 44a of a valve assembly 44 at the bottom of handle 12a of housing 12 and then extends through notches 45 along the interior of the left side of housing 12, and a groove 40c along rod spreader 40. The other end of the tube 42 is then mounted in a hole 48a through a gasket member 48. Gasket member 48 further has two holes 48b and 48c through which rods 14 and 15, respectively, extend. A cross-section of shaft through gasket member 48 is shown in FIG. 7. The gasket member 48 may be made of medical grade rubber, such as Santoprene.

A longitudinal guide member 50 is provided having multiple tracks along its length, including two rod tracks 50a and 50b for rods 14 and 15, respectively, and a guide wire track 50c for the guide wire when extending through instrument 10. These tracks are best shown in the cross-section of FIG. 8 of the shaft through guide member 50. The guide member 50 may be made of extruded flexible material, such as Tecoflex®.

A rigid tube 52 is provided which is D-shaped at one end 52a is registered into a corresponding shaped opening in adapter 38, and a threaded nut 54 having an opening which extends over mounting tube 52 and screws onto the end 39 of the adapter 48 to secure tube 52 to housing 12. With the gasket member 48 loaded first into rigid tube 52, guide member 50 extends from the gasket member 48 through the rigid tube. In this manner, tracks 50a, 50b, and 50c each form a channel with the interior surface of rigid tube 52. Rigid tube 52 may be made of stainless steel, or other rigid material, and has for example, rigid tube 53 has an outside diameter of 5 mm inches. Inside rigid tube 52, gasket member 48 has a ring 48d which frictionally engages the interior surface of tube 52, hole 48a of the gasket member is of a diameter such that the tube 42 tightly fits therein and provides a seal around tube 42. The tube 42 may be held in place in hole 48a by friction, but adhesive may also be used. The rods 14 and 15 are movable back and forth through their respective openings of the gasket 48 and along tracks 50a and 50b.

Figure 10:
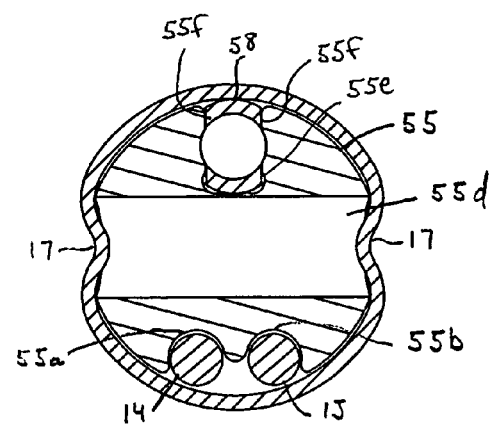
FIG. 10 is a cross-sectional view along lines 10-10 of the instrument of FIG. 4.

Rigid tube 52 exits opening 12e of housing 12 to the distal end 13a, and defines the exterior of shaft 13. A tube coupler 55 in provided in tube 52 at the distal end 13a before the distal opening 13b. Coupler 55 is captured (or attached) in tube 52 by pressure stakes from the outside of tube 52 along two opposing points 17 into openings of a transverse hole 55d of coupler 55, as best shown in FIG. 10. Tube coupler 55 has two longitudinal channels 55a and 55b through which rods 14 and 15 extend and are movable back and forth therein. Two opposing pockets along the exterior of coupler 55 may be used for attachment to tube 52 rather than through hole 55d. Tube coupler 55 has another longitudinal channel 55e having opposing flat sides 55f. A guide tube 58 is provided at the distal end 13a of the instrument. The guide tube 58 is cut to provide two opposing longitudinal openings 59 about which the width of the tube 58 is reduced such that it frictionally engages opposing flat sides 55f when located in channel 55e of coupler 55.

Figure 5:
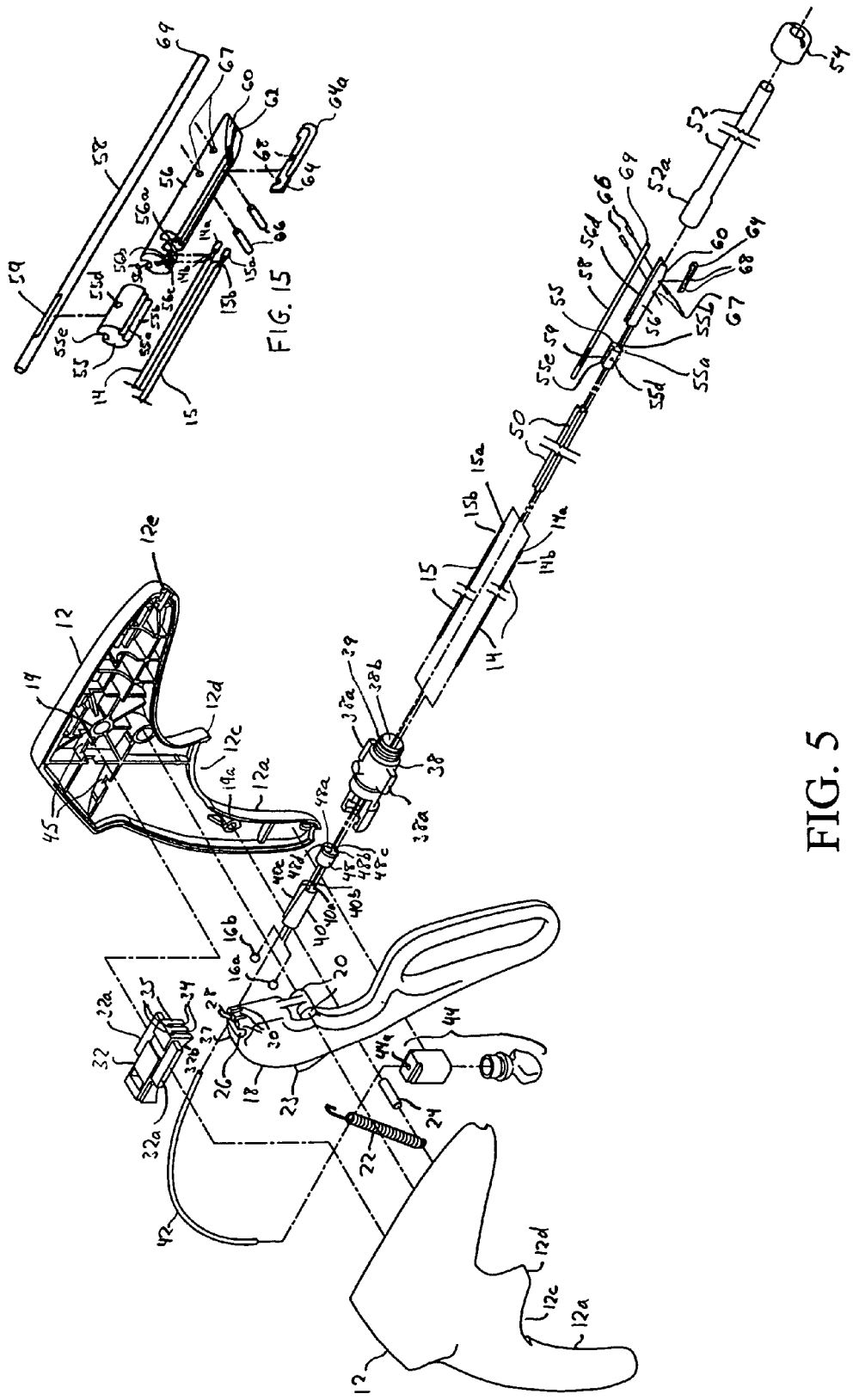
FIG. 5 is an exploded perspective view of the instrument of FIG. 1.
Figure 9:
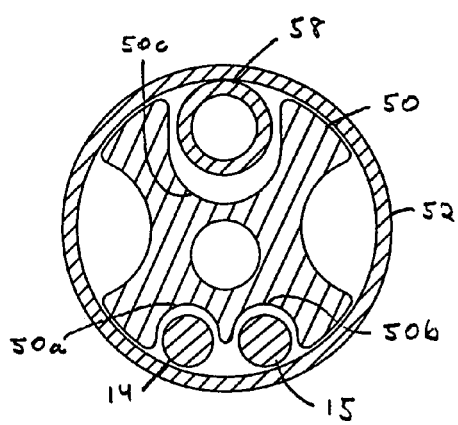
FIG. 9 is a cross-sectional view along lines 9-9 of the instrument of FIG. 4.
Figure 11:
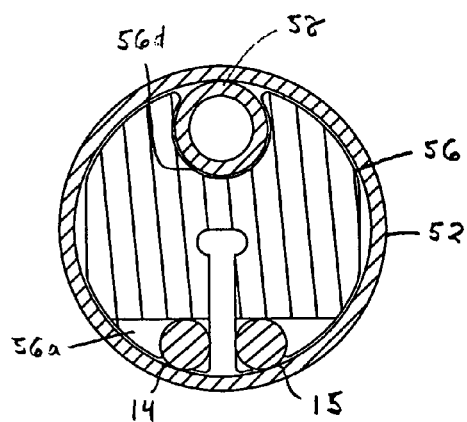
FIG. 11 is a cross-sectional view along lines 11-11 of the instrument of FIG. 4.
Figure 10A:
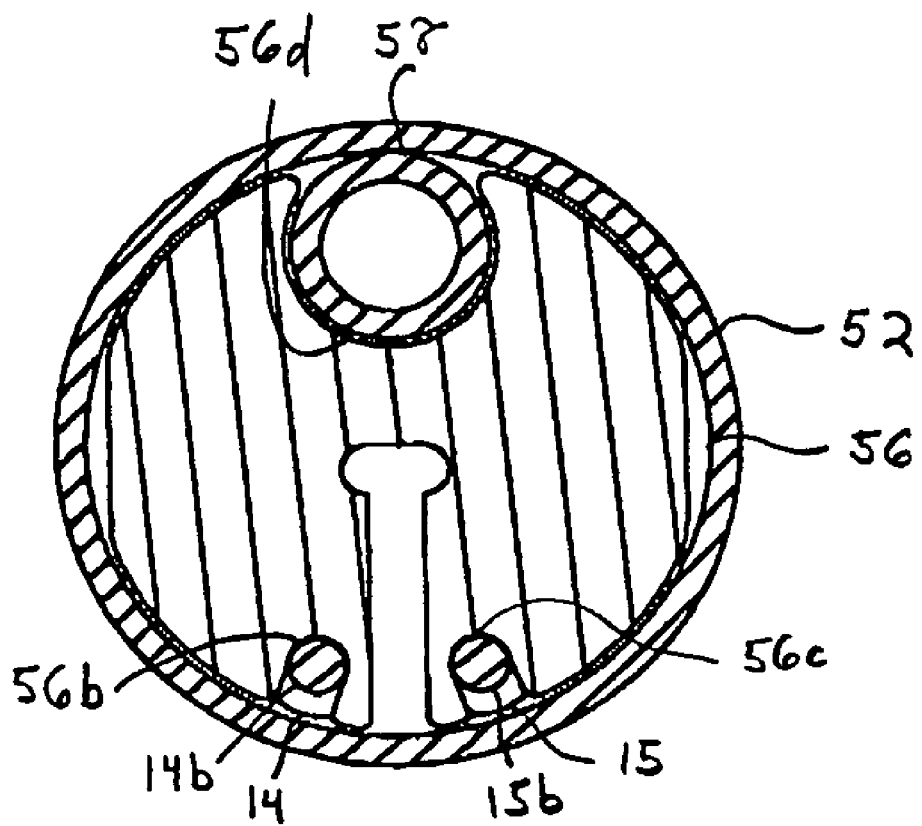
FIG. 10A is a cross-sectional view along lines 10A-10A of the instrument of FIG. 4.
Figures 16, 16A:
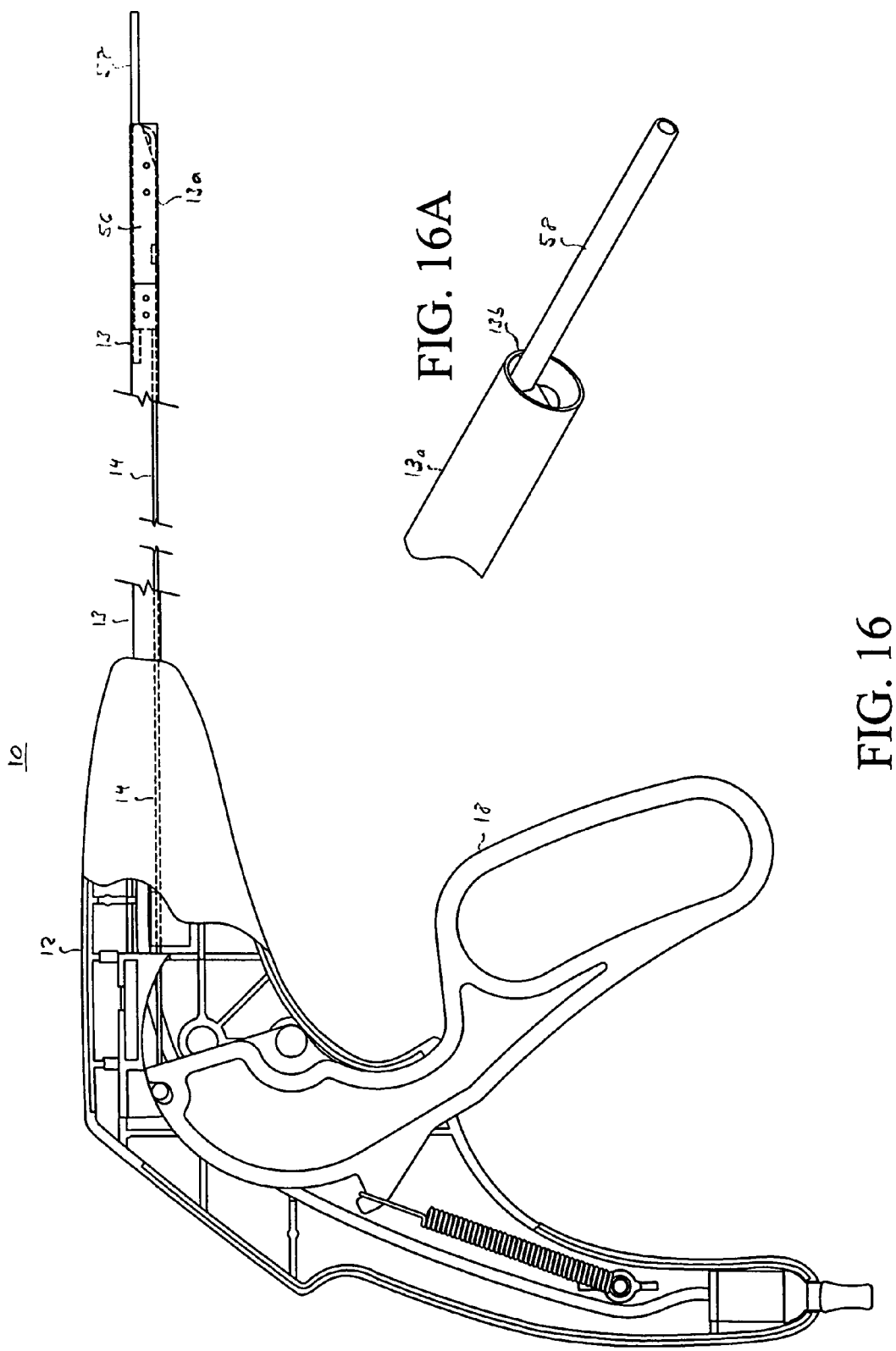
FIG. 16 is a partial detailed view of the actuator member controlled drive mechanism of the instrument of FIG. 1 with the actuator member fully forward and the blade shuttle fully retracted back into the shaft of the instrument in which the guide wire of FIG. 1 is shown removed.
FIG. 16A is a perspective view of the distal end of the instrument in FIG. 16 showing the blade shuttle and blade fully retracted back in the instrument.
Figures 17, 17A:
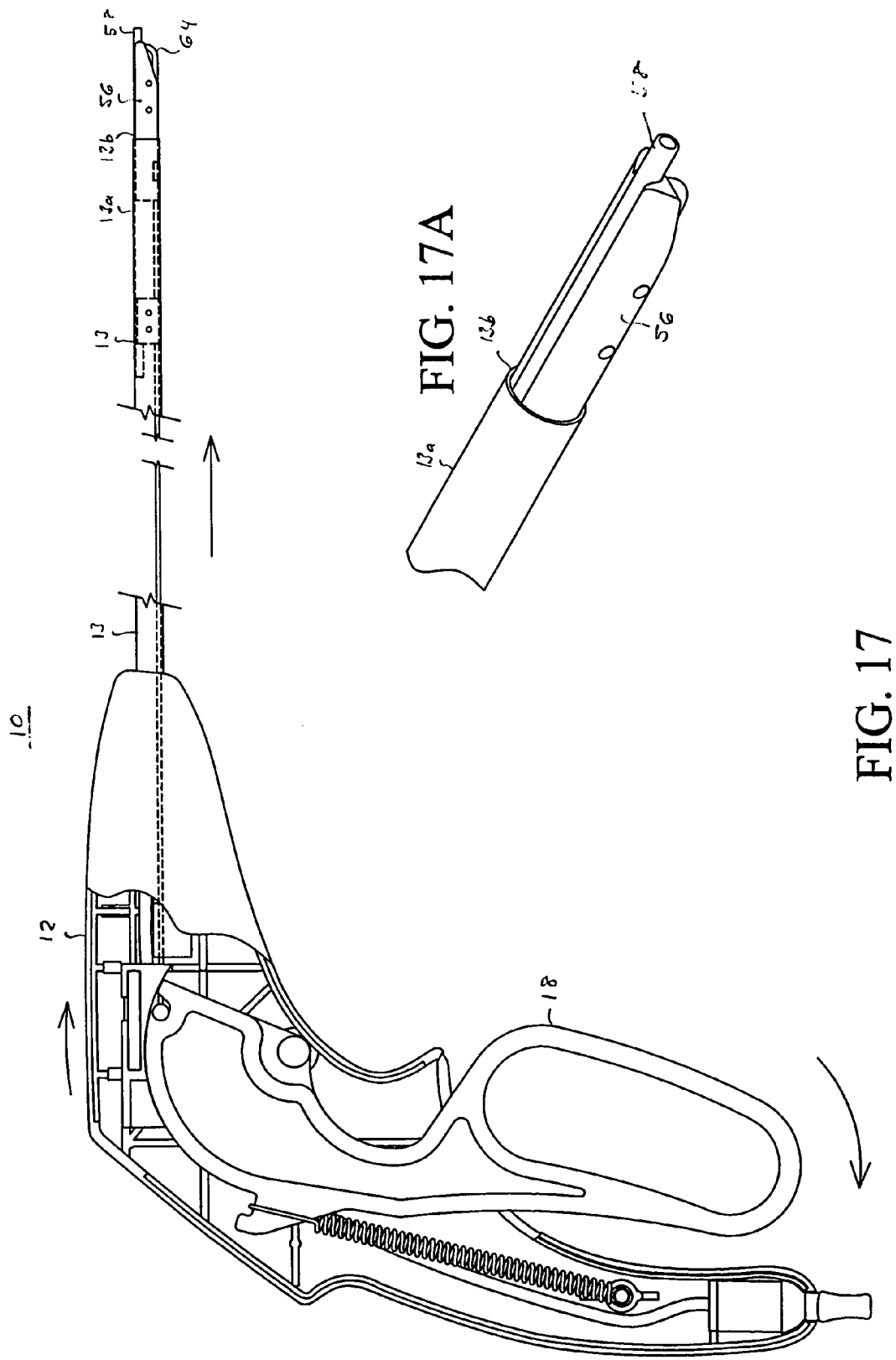
FIG. 17 is a partial detailed view of the actuator member controlled drive mechanism of the instrument of FIG. 1 with the actuator member fully back and the blade shuttle fully advanced out over the guide tube in which the guide wire of FIG. 1 is shown removed.
FIG. 17A is a perspective view of the distal end of the instrument in FIG. 17 showing the blade shuttle and blade fully advanced.

As best shown in FIGS. 5, 10A, 11, and 15, at the distal end 13a drive rods 14 and 15 before their ends 14a and 15a, respectively, have a reduced diameter region 14b and 15b, respectively (FIG. 5). A blade shuttle 56 has an opening 56a and two slots 56b and 56c extending to opening 56a (FIG. 15). The slots 56b and 56c are sized to receive reduced diameter regions 14b and 15b, respectively, such that ends 14a and 15b lie in opening 56a thereby attaching blade shuttle to the rods. Blade shuttle 56 has a channel 56d through which guide tube 58 is located. Blade shuttle 56 is movable longitudinally back and forth along the guide tube, which lies stationary in the distal end. The proximal end of guide tube 58 extends partially into channel 50c of the guide member 50 to prevent rotation of the guide tube at its most distal end 69 (FIG. 9), which extends through distal opening 13b, as shown in FIGS. 1 and 1A. The guide tube 58 extends, via opening 13b, from the distal end 13a, such as for example 0.9 inches. The blade shuttle 56 may be made of metal by electrical discharge machining (EDM) process, or of molded plastic. A cross-section of blade shuttle 56 where rods 14 and 15 terminate in opening 56a is shown in FIG. 11, and after rods 14 and 15 terminate in FIG. 12.

Blade shuttle 56 has a slanted surface 60 with a slot 62 into which a blade 64 is received such that its sharp edge 64a extends out slot 62 (FIG. 14). The blade 64 is held in the blade shuttle 56 by two pins 66 through holes 67 in the blade shuttle and through holes 68 in blade 64 (FIG. 13). When assembled, the integrated blade shuttle 56 and blade 64 is extendable and retractable through distal opening 13b (i.e., end of tube 52) of the instrument 10 in response to pivoting of actuator member 18 which translate forward or backward motion to the drive rods 14 and 15 and to the blade shuttle 56 and blade 64 guided longitudinally along the outer tubular surface of guide tube 58 riding in channel 56d. FIGS. 1 and 1A show the integrated blade shuttle and blade retracted in distal end 13a, and FIGS. 2 and 2A show the integrated blade shuttle and blade extended. As shown in these figures, a guide wire 70 is passed into open end 69 of guide tube 58, via an opening extending through the guide tube to the other end of the guide tube, along a path through the instrument provided by channel 50c of guide member 50, opening 48a of gasket 48, into and through routing tube 42, and through an opening 44a extending through valve assembly 44, and exiting the instrument. Valve assembly 44 has a valve control 44b which can be turned to open and closed opening 44a, and may be the same or similar to the valve assembly described in U.S. patent application Ser. No. 09/776,431, filed Feb. 2, 2001, now U.S. Pat. No. 6,997,931, or International Patent Application PCT/US02/02791, published under International Publication No. WO 02/062200 A2. The valve assembly 44 extends through an opening 12f in handle 12. Optionally, the valve assembly 44 may be removed from instrument 10, and routing tube 42 extended to opening 12f, which is sized to engage the end of tube 42.

Figure 3:
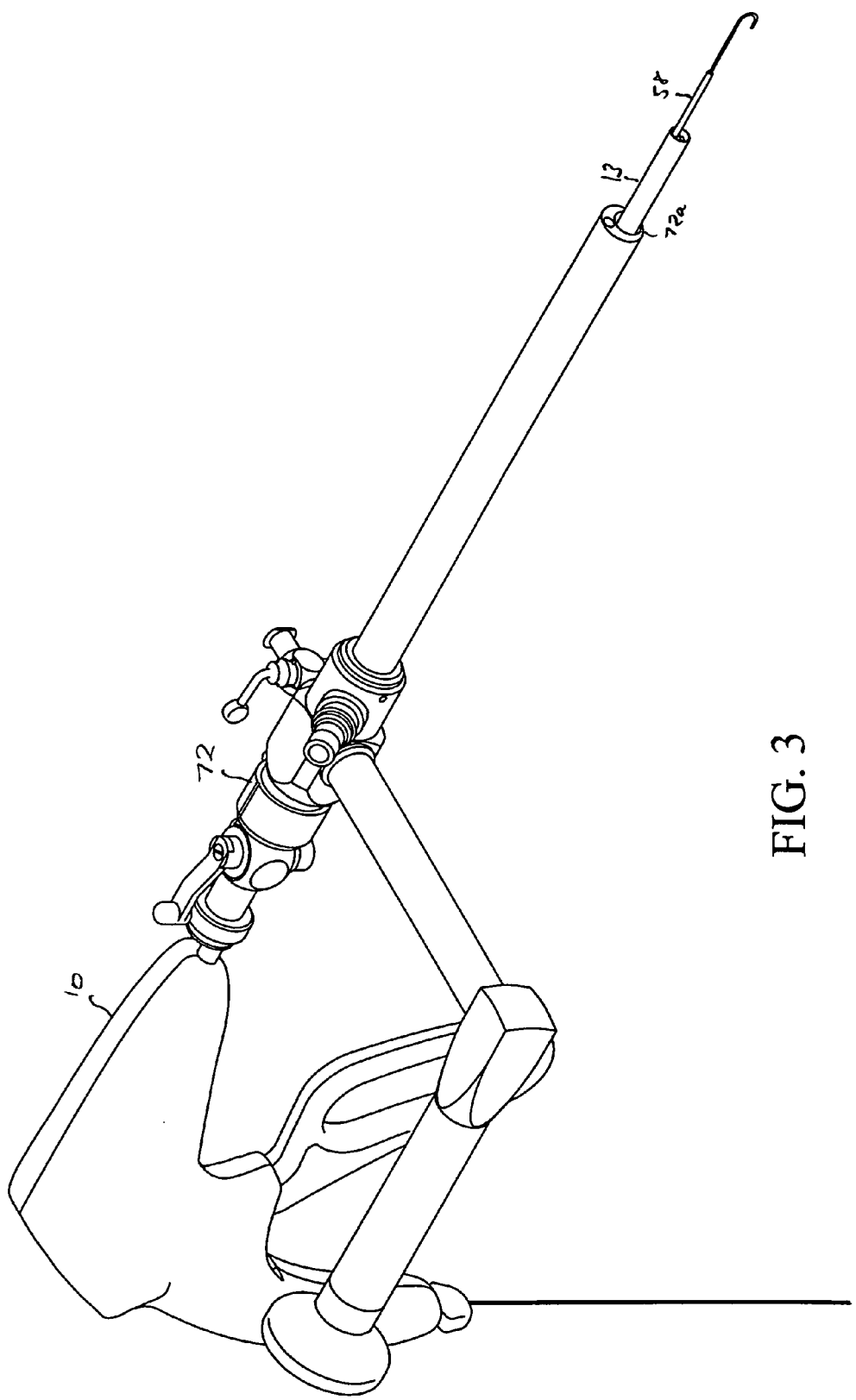
FIG. 3 is a perspective view of the instrument of FIGS. 1 and 2 when inserted through the working channel of a nephroscope.
Figure 4:
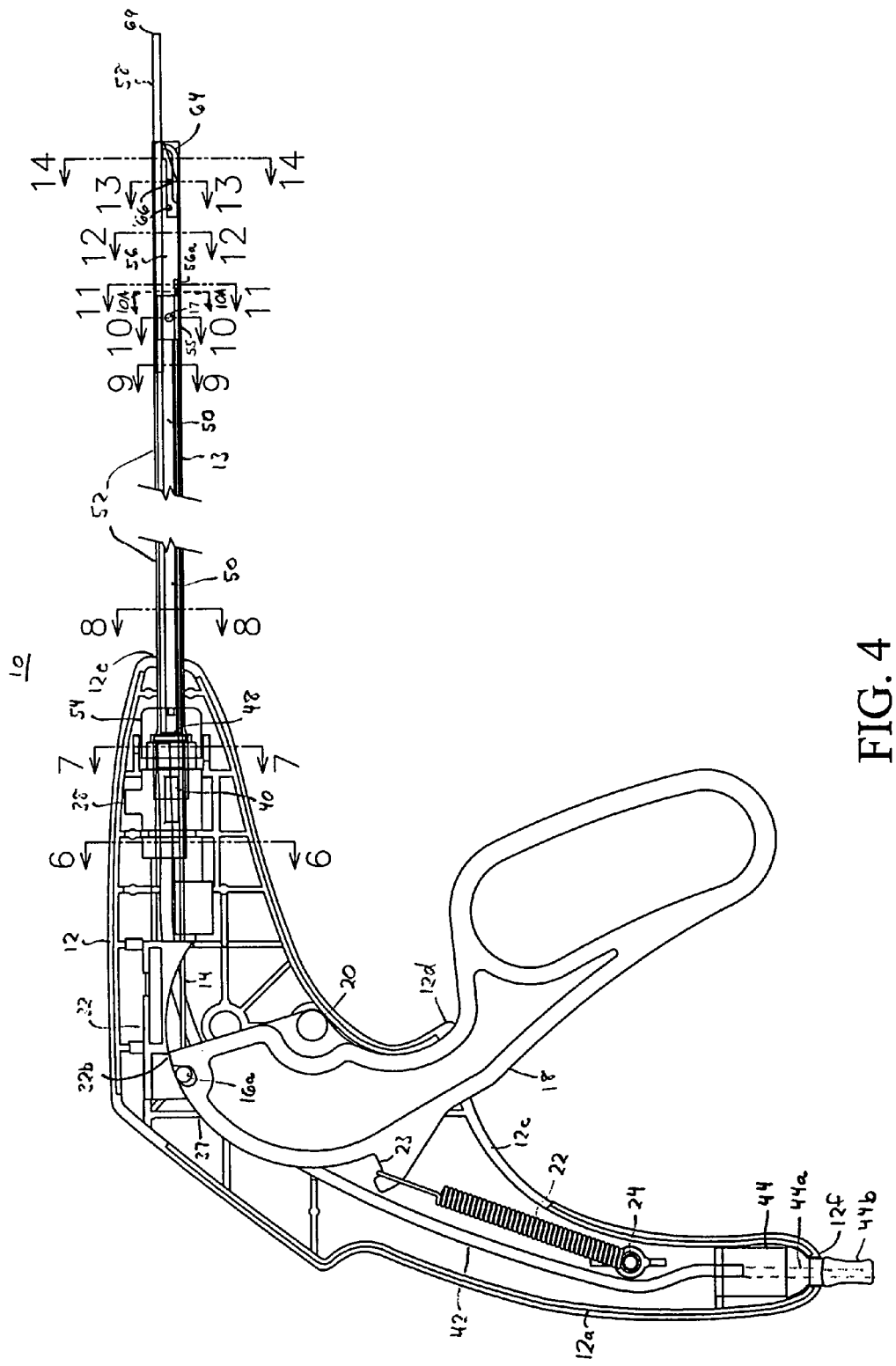
FIG. 4 is a schematic side view of the instrument of FIG. 1.

The shaft 13 of the instrument 10 is preferably sized to pass through a channel, such as the working channel 72a of an endoscope, such as a nephroscope 72 shown in FIG. 3. Nephroscope 72 may be a typical nephroscope having an optical system to view the operation of the instrument 10. However, the instrument may be used with other imaging systems for laproscopic or other surgical procedures, or without an endoscope. When passed through an endoscope, the blade shuttle 56 is in its retracted position in the distal end 13a of the shaft, which shields blade 64 for transmission through an endoscope's working channel.

Figure 18:
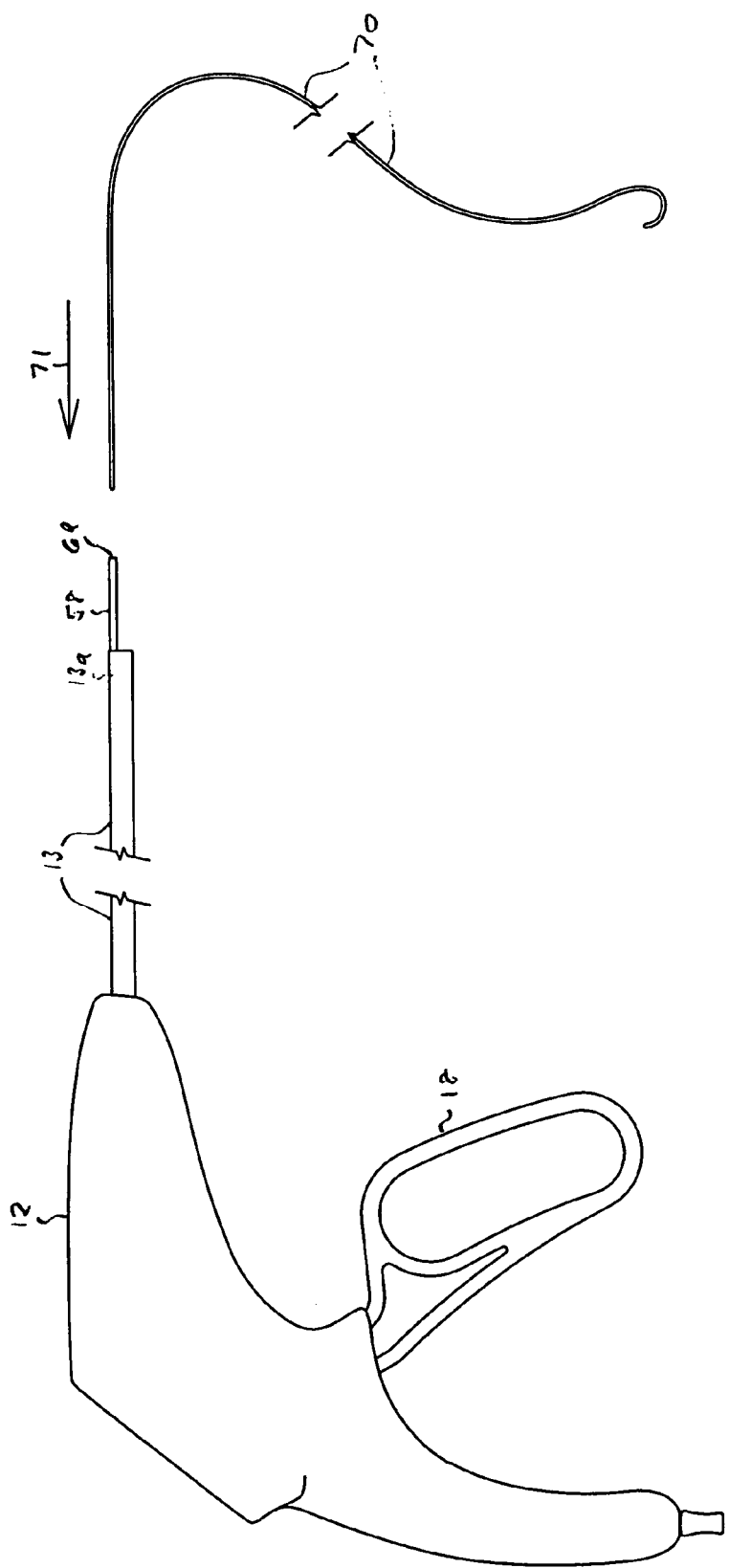
FIG. 18 is a side view of the instrument of FIG. 1 prior to guide wire loading.
Figure 19:
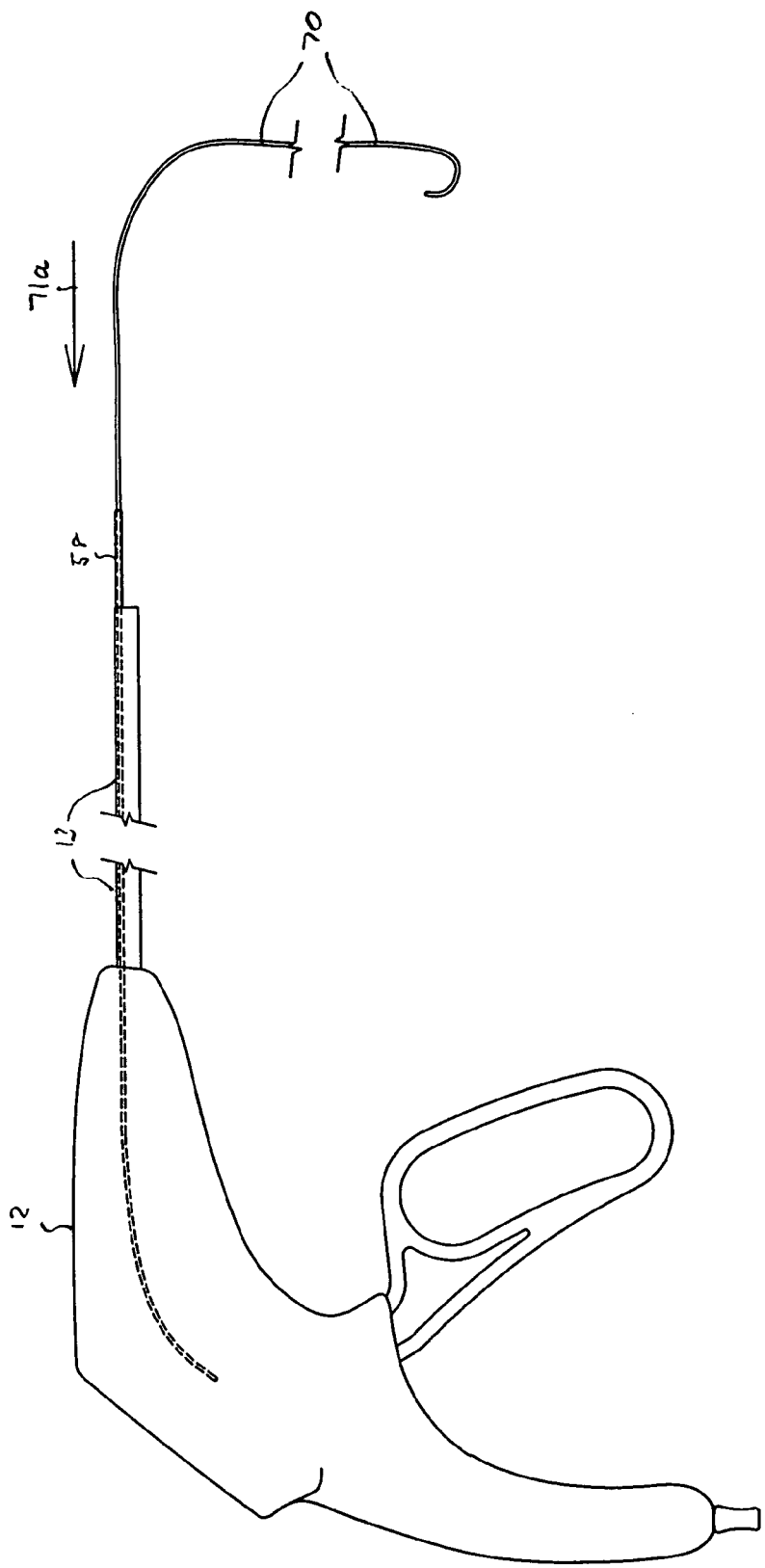
FIG. 19 is a side view of the instrument in FIG. 1 with the guide wire partially loaded through the instrument.
Figure 20:
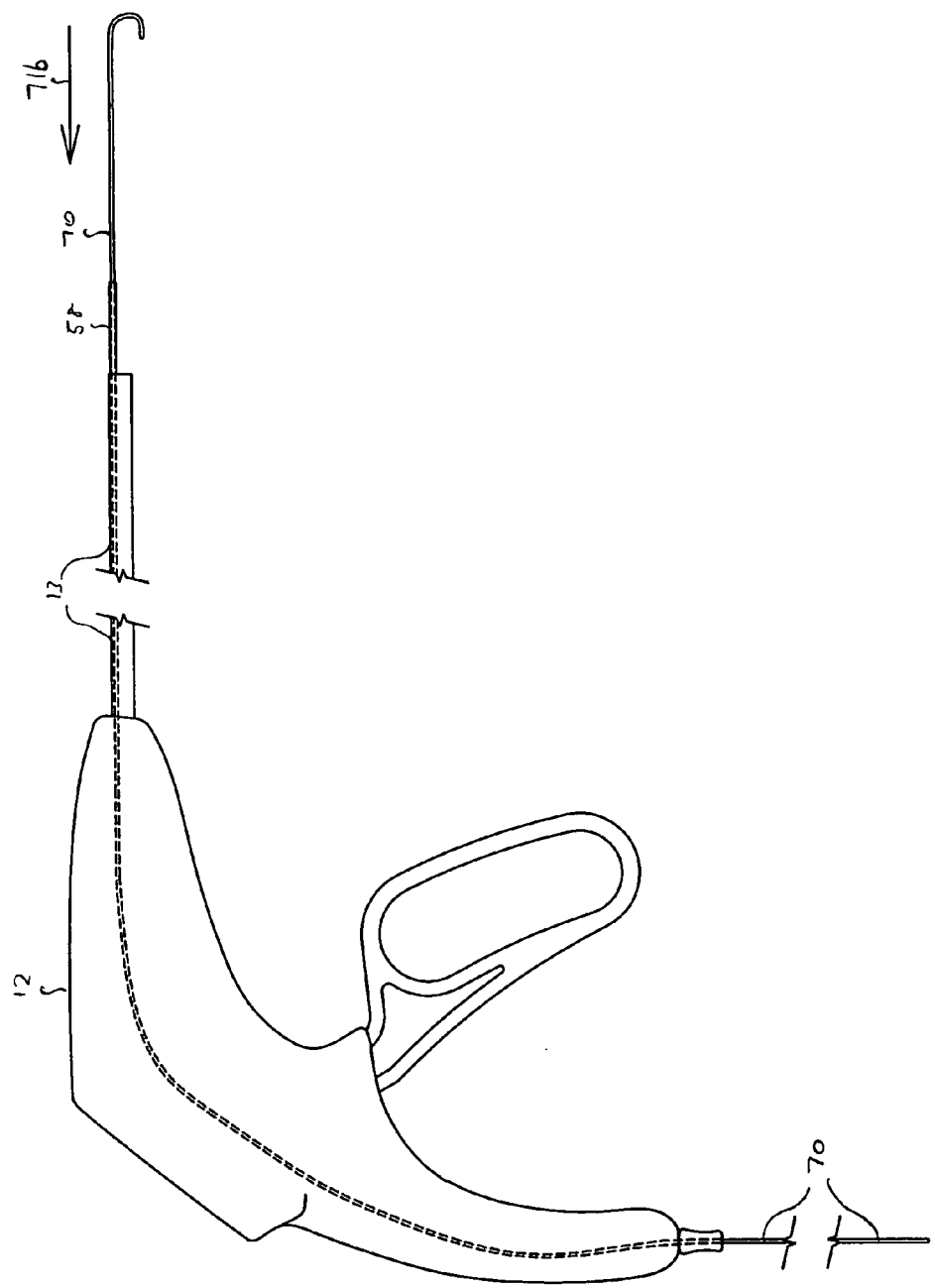
FIG. 20 is a side view of the instrument of FIG. 1 showing the guide wire completely loaded through the instrument and exiting both ends of the instrument.
Figure 21:
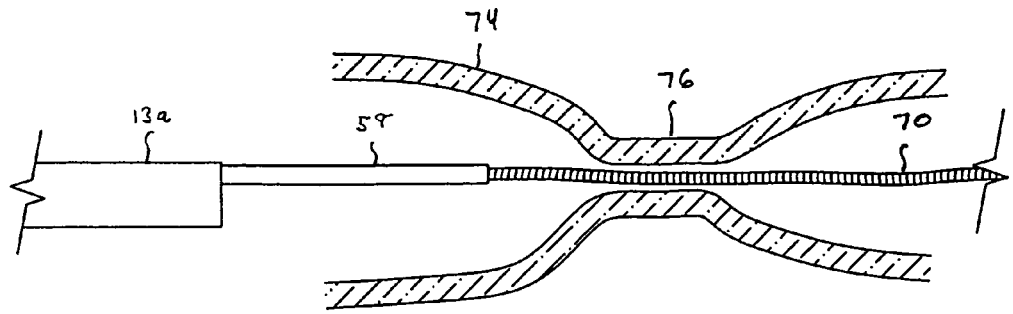
FIG. 21 is a schematic partial view of the distal end of the instrument of FIG. 1 with a guide wire through a narrow section of a tubular tissue structure (shown in cross-section) and with the guide wire inside of the guide tube on the proximal side of the stricture.
Figure 22:
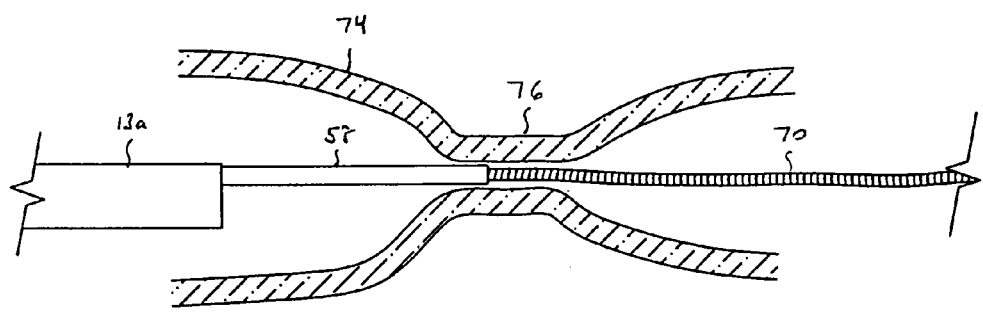
FIG. 22 is a schematic partial view of the distal end of the instrument of FIG. 1 showing the tube guide entering over the guide wire the stenotic region of the tubular tissue structure of FIG. 21.
Figure 23:
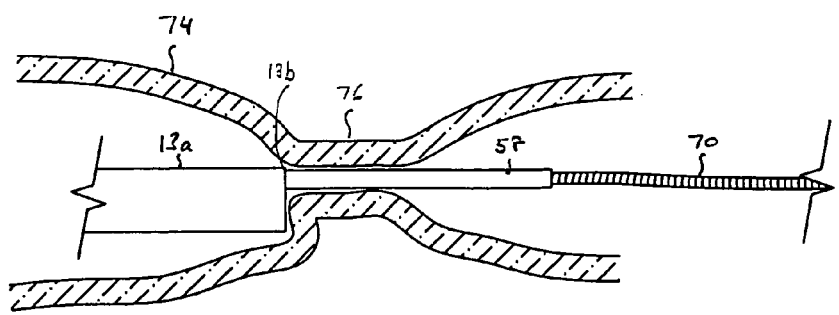
FIG. 23 is a schematic partial view of distal end of the instrument of FIG. 1 showing the shaft of the instrument abutting the stenotic region of FIG. 22 and the guide tube completely through the stenotic region.
Figure 24:
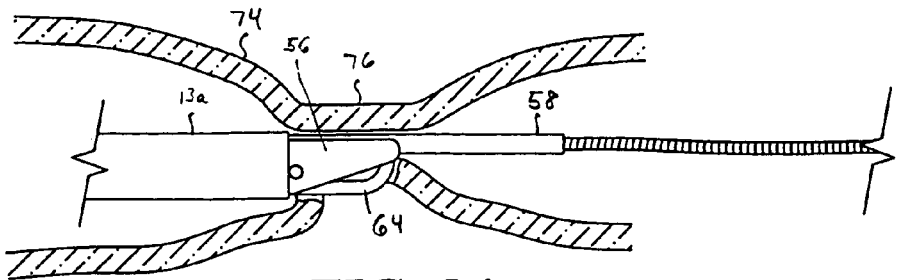
FIG. 24 is a schematic partial view of the distal end of the instrument of FIG. 1 showing the blade shuttle and blade partially advanced over the guide tube and the blade cutting the wall of the tubular tissue structure of FIG. 23.
Figure 25:
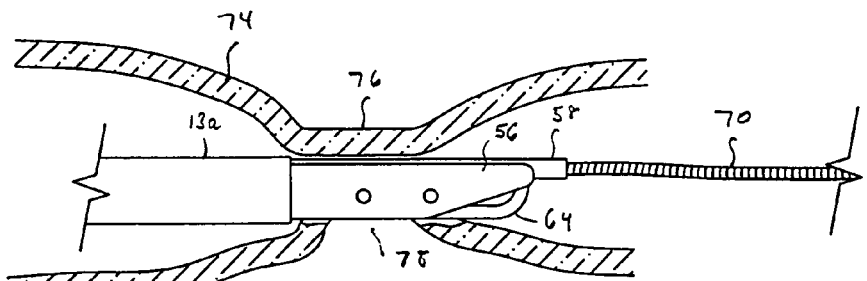
FIG. 25 is a schematic partial view of the distal end of the instrument of FIG. 1 showing the blade shuttle fully advanced over the guide tube and the blade fully advanced with the longitudinal incision completed in the structure of the tubular tissue structure of FIG. 24.
Figure 26:
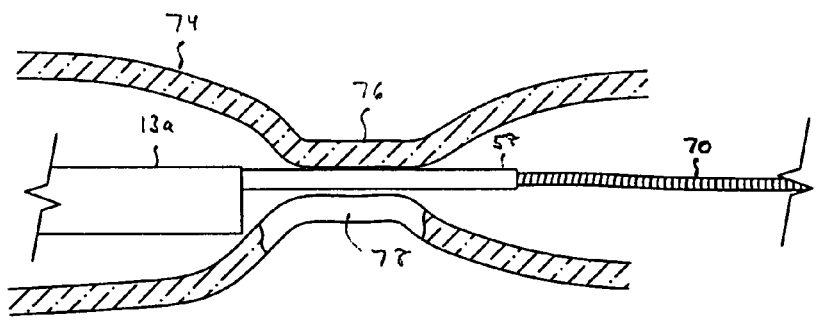
FIG. 26 is a schematic partial view of the distal end of the instrument of FIG. 1 showing the blade shuttle and blade retracted fully back in the instrument just prior to the guide tube's withdrawal from the stricture of FIG. 25.
Figure 27:
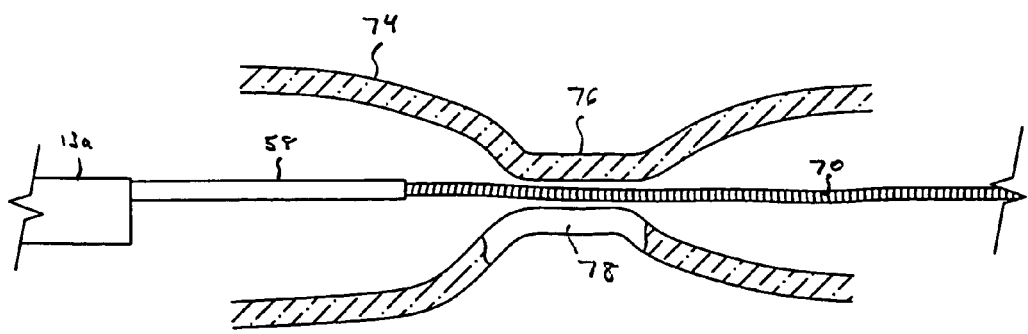
FIG. 27 is a schematic partial view of the distal end of the instrument of FIG. 1 showing retraction of the instrument away from the incision site in the tubular structure of FIG. 26 whereby the guide wire is kept in place.

Referring to FIGS. 18-38, the operation of the instrument 10 is shown in which a guide wire 70 has already been passed through the tubular tissue structure 74, such as the ureter of a patient, and a stenotic (narrowing) region 76 thereof. First, a guide wire 70 is loaded into the guide tube 58 and through the instrument. FIG. 18 shows the guide wire 70 before loading in instrument 10, where the direction of the guide wire is indicated by arrow 71. FIG. 19 shows the guide wire 70 partially loaded in instrument 10, where the direction of the guide wire is indicated by arrow 71a. FIG. 20 shows the guide wire 70 passed through the instrument 10, where the direction of the guide wire is indicated by arrow 71b. With the guide wire 70 now loaded, the distal end 13a of the instrument is guided by the guide wire 70 through a narrow section 76 of a tubular tissue structure 74 (shown in cross-section in FIGS. 21 and 22), and with the guide wire 70 inside of the guide tube 58 through the stenotic region 76, as shown in FIG. 23. Next, the blade shuttle 56 with blade 64 is advanced over the guide tube 58 and the blade 64 cuts the wall of the narrow region 76 of tube 74 to provide a longitudinal incision 78, as shown in FIGS. 24 and 25, by a user pulling on actuator member 18 towards handle portion 12a to translate forward linear motion to the blade shuttle and blade guided by the guide tube and the guide wire therein. The blade shuttle is mechanically coupled to the actuator member, as describe earlier. As illustrated in FIG. 24, the depth of the cut is controlled by the height of blade 64 from the blade shuttle 56, while the length of the cut is controlled by the extent the actuator member 18 is pulled by the user to a maximum length based on maximum travel distance of the blade shuttle 56 from distal end 13a. After the cut in complete, the blade shuttle 56 and blade 64 is then retracted fully back into distal end 13a, as shown in FIG. 26, by the user releasing the actuator member 18 away from handle portion 12a to translate reverse linear motion to the blade shuttle 56 and blade 64. The instrument 10 is then retracted from the incision site in the stenotic region 76, as shown in FIG. 27, and withdrawn from the tubular structure 74 leaving the guide wire 70 in place. If a longer stenotic region 76 than shown in the figures is present, the instrument 10 can be placed again over the guide wire 70 through the remaining stenotic region 76 and another incision can be made as described above.

Valve assembly 44 may be open when the guide wire 70 is loaded in the instrument 10 through valve opening 44a, but closed by turning valve control 44b (FIG. 4) with the guide wire extending through valve opening 44a, when the guide tube 58 nears (or is adjacent to) the tissue site to be cut, and then opened when the instrument is retracted away from the tissue site. The valve allows the guide wire 70 to be drawn under slight tension through the valve, if needed. Other types of valve assemblies 44 may alternatively be used which enables the guide wire to be drawn under slight tension through the valve. Optionally, the valve assembly may be removed from housing 12, or if the valve is present, may remain open throughout the procedure, or if desired, the guide wire 70 may be advanced through the closed valve when the instrument is loaded in the patient and during the procedure.

An example of the longitudinal incision (or wound) 78 in a tubular structure resulting from the cut made by instrument 10 is shown in FIG. 28. The incision results in a wound which may then be closed by stitches of suture. Arrows 73 in FIGS. 28, 29, and 30, indicate the direction of pulling the proximal and distal margins or ends 80a and 80b, respectively, of the longitudinal incision 78 together to provide for more luminal diameter 75 in response to placement of stitches 81. FIG. 30 shows stitches 81 may then be placed on opposing wound edges or sides 82a and 82b to provide a sutured closure of the tubular structure to add increased diameter at the expense of structure length. Alternatively, the tissue incised by the instrument 10 may be left to heal without mechanical closure, rather than being mechanically closed to appose wound edges for the induction of primary healing.

One use of the instrument 10 is to apply an incision in the ureteropelvic junction (UPJ) of a patient's ureter via a percutaneous renal access. The percutaneous renal access is typically established through inserting a needle with a guide wire through the kidney and subsequently into the renal pelvis. Serial mechanical dilation or balloon dilation through the skin into the kidney and pelvis permits placement of a sheath for communication between the outside and the renal pelvis. After establishing the sheath as a working conduit, a UPJ stricture can be incised using the instrument 10. The nephroscope is passed through the sheath to view the ureter pelvic junction. The instrument along with its guide wire is passed through the nephroscope directed towards the inferior pole of the kidney, as shown in FIG. 3. When the narrowed urethral opening is viewed, the guide wire from this instrument can be passed through the constricted segment of the urethra down through the ureter and into the bladder. Next, the instrument's guide tube 58 can be advanced through the stenotic region of tissue up until the distal end 13*a* of the shaft abuts against the narrowed ureteral opening (or to any lesser depth as desired). The user can press the guide tube 58 toward the desired side of the incision (usually the posteriolateral side of a stenotic ureter). Squeezing the actuator member 18 drives the blade shuttle 56 forward to cut the tissue. For example, the depth of this cut may be approximately 2.5 mm over the desired length, and such length of the cut may be a maximum of 18 mm. As stated earlier, the particular cutting path length depends on the extent of forward movement of the blade shuttle and blade from distal end 13*a* to its maximum extent from distal end 13*a*. An incision of approximately 2 cm, but not more than 3 cm, was required in the porcine models tested at the Cleveland Clinic Foundation as published in the earlier cited article in *Journal of Endourology*. If a longer stenotic region is needed upon further review of the wound site, such as via images from a nephroscope, the instrument 10 can be placed again over the guide wire 70 through the remaining stenotic region and a second (or more) incision can be made as desired. Release of the actuator member 18 retracts the blade shuttle 56 safely back into the shaft 13 of the instrument. The instrument 10 along with the guide tube 58 is pulled from the urinary pelvic junction, leaving the guide wire still traversing the ureter at the incision site. The wound site can be inspected for adequacy of length via nephroscope images. If the suture closure of the wound site is desired, the site can be further manipulated with surgical graspers or cautery tools to mobilize the wound and prepare for suturing.

The above operation of the instrument 10 to apply an incision in the ureteropelvic junction of the ureter of a patient is illustrated in FIGS. 31-38. These figures show a view of the instrument's distal end 13*a* as provided by typical imaging means of a nephroscope to a user. First, a guide wire 70 is placed through the ureteropelvic junction of ureter 84. FIG. 31 shows the guide wire 70 extending out the ureteral opening of the ureteropelvic junction. The guide tube 58 of the instrument 10 is then advanced over a guide wire 70 toward the ureter 84, as shown in FIG. 32. Next, the guide tube 58 is passed over the guide wire 70 about to enter the ureter 84, as shown in FIG. 33. The guide tube 58 then enters the ureter 84, as shown in FIG. 34. While the distal end 13*a* of the shaft abuts against the proximal ureteral opening, the blade shuttle 56 and blade 64 are advanced and retracted to make an incision 85, as shown in FIGS. 35 and 36 where the blade shuttle and blade are blocked from view. The guide tube 58 exits the incised ureter 84, as shown in FIG. 37, and the instrument 10 is retracted from the site leaving the guide wire 70 in the incised ureter 84, as shown in FIG. 38.

Alternatively, a drive tube rather than drive rods may be used which is mounted at one end to the top of the actuator member, extends through the shaft, and couples at its other end to the blade shuttle and blade. Further, the shaft may be flexible as described in the above-cited U.S. patent application Ser. No. 09/776,431 or International Patent Application No. PCT/US02/02791, which are incorporated herein by reference.

Although the instrument 10 has been described for use in narrowed region of a tubular structure at remote sites in the body of a patient, such as in the urinary tract, biliary tract, gastrointestinal structures or along any tissue surface or soft tissue structure in the body, it may also be used for cutting tissue for biopsy specimens, or other surgical applications where longitudinal incisions are needed.

From the foregoing description, it will be apparent that an instrument and method is provided for guided surgical cutting of tissue. Variations and modifications in the herein described apparatus and method in accordance with the invention will undoubtedly suggest themselves to those skilled in the art. For example, although the instrument is directed for use in tubular structures, it may be used in other surgical application where remote cutting of tissue is required. Accordingly, the foregoing description should be taken as illustrative and not in a limiting sense.

The invention claimed is:

1. An instrument for cutting tissue guided along a guide wire comprising:
    a proximal end having a housing;
    a shaft extending from said housing to a distal end of the instrument, said shaft having at said distal end an opening to outside of said instrument;
    a guide tube extending from said shaft through said opening of said shaft in which said guide tube comprises an outer tubular surface, two ends, and an opening extending through said guide tube between said ends of said guide tube;
    a path through at least said opening of said guide tube; a guide wire extendable along at least said path; and
    means for longitudinally cutting tissue guided along the outer tubular surface of said guide tube through said opening of said shaft, said means comprising a blade extendable and retractable through said opening of said shaft to cut tissue when present outside of said instrument, wherein said longitudinally cutting means further comprises a blade shuttle attached to said blade having a longitudinal channel within which said guide tube is located to linearly guide said blade shuttle travel along the outer surface of said guide tube.

2. The instrument according to claim 1 wherein said longitudinally cutting means provides a cut of a predetermined depth and width.

3. The instrument according to claim 1 wherein said longitudinally cutting means further comprises means at said housing coupled to said blade for remotely controlling the extending and retracting of said blade at said distal end.

4. The instrument according to claim 1 wherein said longitudinally cutting means further comprises:
    a pivotal actuator member at said housing; and
    one or more drive rods or tubes each having a distal end coupled to said blade shuttle and a proximal end coupled to said actuator member in which pivoting of said actuator member controls said extending and retracting of said blade shuttle.

5. The instrument according to claim 1 wherein when a guide wire is extended along said path, said distal end is located adjacent tissue along said guide wire to be cut when said blade is extended.

6. The instrument according to claim 1 wherein said shaft is extendable through an endoscope.

7. The instrument according to claim 1 wherein said shaft is rigid or at least partially flexible.

8. The instrument according to claim 1 wherein said shaft is positionable in a tubular tissue structure through which said distal end of the instrument is guided by the guide wire along the path for extending said guide wire, and said blade when extended provides the longitudinally incision along a narrowed region of the tubular structure.

9. The instrument according to claim 1 wherein said guide tube is non-movable with respect to said shaft.

10. The instrument according to claim 1 wherein said path for extending the guide wire extends through said housing, said shaft, and said guide tube, and then exits said guide tube.

11. The instrument according to claim 1 wherein said blade is external of said guide tube and has a single longitudinally oriented sharp edge, and said means disposes said blade to extend longitudinally along the outer tubular surface of said guide tube through said opening of said shaft to enable said edge of said blade to make a longitudinal incision in tissue when present outside of said instrument.

12. An instrument for cutting tissue guided along a guide wire comprising:
   a shaft extending to a distal end of the instrument, said shaft having an opening at said distal end;
   a guide tube at said distal end having an outer tubular surface which extends through said opening in which a guide wire is receivable through said guide tube; and
   a movable blade shuttle comprising a blade, and a longitudinal channel receiving said guide tube to enable said guide tube to linearly guide said blade shuttle travel riding along the outer tubular surface of said guide tube in said channel when said blade shuttle is extended from said opening or retracted back through said opening, wherein said guide tube extends through said opening of the shaft beyond said shaft and said blade shuttle when retracted, to define a path along which said blade shuttle is extendable and retractable.

13. The instrument according to claim 12 further comprising a housing coupled to said shaft and means for remotely controlling movement of said blade shuttle at said distal end to cut tissue.

14. The instrument according to claim 12 further comprising:
   a housing coupled to an end of said shaft opposite said distal end;
   a pivotal actuator member at said housing; and
   one or more drive rods or tubes each having a distal end coupled to said blade shuttle and a proximal end coupled to said actuator member in which pivoting of said actuator member controls said extending and retraction of said blade shuttle via said opening.

15. The instrument according to claim 12 further comprising a pathway through at least said guide tube and said shaft for extending a guide wire.

16. The instrument according to claim 15 wherein said guide wire is extended along said pathway to locate said distal end of the instrument adjacent the tissue to be cut by said blade, and said blade shuttle is extended and retracted along said path to enable said blade to extend outside said instrument to cut said tissue.

17. The instrument according to claim 12 wherein said guide tube is non-movable with respect to said shaft.

18. The instrument according to claim 12 wherein said blade is external of said guide tube and has a sharp edge, and said blade shuttle longitudinally travels along the outer tubular surface of said guide tube through said opening of said shaft to enable said edge of said blade to make a longitudinal incision in tissue when present outside of said instrument.

19. An instrument for guided cutting of tissue comprising:
   a housing; a shaft extending from said housing to an end; a blade at said end movable to extend out of said shaft to cut tissue when present outside of said instrument; a guide member which guides movement of said blade at said end out of said shaft, wherein said guide member has an opening through which a guide wire is receivable, and said guide member is non-movable with respect to said shaft, and said blade is movable with respect to said guide member; and a shuttle external of said guide member having a slot retaining said blade, in which shuttle rides along said guide member to extend said blade from said shaft and to retract said blade back into said shaft.

20. The instrument according to claim 19 wherein said member has an outer surface and said blade is guided along said outer surface of member outside said shaft.

21. The instrument according to claim 20 wherein said outer surface of said member represents a tubular outer surface.

22. The instrument according to claim 19 wherein said shaft has an opening to outside of said instrument, and said blade extends out of said shaft through said opening to cut tissue outside of said instrument which neighbors said guide member.

23. The instrument according to claim 19 wherein said guide member represents a tube, said opening extends through said tube, and said instrument further comprises a path through at least said guide tube for extending said guide wire.

24. The instrument according to claim 19 further comprising means coupled to said shaft for remotely controlling movement of said shuttle.

25. The instrument according to claim 19 wherein said blade is non-tubular.

* * * * *